US012560301B2

(12) United States Patent     (10) Patent No.:   US 12,560,301 B2

Van Bommel     (45) Date of Patent:     Feb. 24, 2026

(54) DISINFECTION LIGHTING DEVICE HAVING BATWING OPTICS

(71) Applicant: SIGNIFY HOLDING B.V., Eindhoven (NL)

(72) Inventor: Ties Van Bommel, Horst (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/992,207

(22) PCT Filed: Jun. 28, 2023

(86) PCT No.: PCT/EP2023/067710
§ 371 (c)(1),
(2) Date: Jan. 8, 2025

(87) PCT Pub. No.: WO2024/008540
PCT Pub. Date: Jan. 11, 2024

(65) Prior Publication Data
US 2026/0009519 A1     Jan. 8, 2026

(30) Foreign Application Priority Data
Jul. 8, 2022    (EP) ..................................... 22183847

(51) Int. Cl.
*A61L 2/08*     (2006.01)
*A61L 2/084*     (2026.01)
(Continued)

(52) U.S. Cl.
CPC ................ *F21V 5/04* (2013.01); *A61L 2/084* (2013.01); *A61L 2/10* (2013.01); *A61L 2/24* (2013.01);
(Continued)

(58) Field of Classification Search
CPC ...... A61L 2/0047; A61L 2/0052; A61L 2/084; A61L 2/10; A61L 9/18; A61L 9/20; A61L 2202/11; A61L 2209/12; F21W 2131/20
See application file for complete search history.

(56) References Cited

U.S. PATENT DOCUMENTS

| | | | |
|---|---|---|---|
| 7,339,200 B2 * | 3/2008 | Amano .................... | F21S 41/14 |
| | | | 257/E33.059 |
| 7,422,347 B2 * | 9/2008 | Miyairi ................... | G09F 13/22 |
| | | | 362/333 |
| 7,798,679 B2 * | 9/2010 | Kokubo .................. | F21V 5/048 |
| | | | 362/334 |

(Continued)

FOREIGN PATENT DOCUMENTS

| | | | | |
|---|---|---|---|---|
| WO | 2022066428 A1 | 3/2022 | | |
| WO | WO-2022078805 A1 * | 4/2022 | ............. | A61L 2/084 |
| WO | WO-2023217824 A1 * | 11/2023 | ........... | A61L 2/0047 |

*Primary Examiner* — Ismael Negron

(57) ABSTRACT

A device including a first solid-state light source configured to emit white light; a second solid-state light source configured to emit violet light having a dominant peak wavelength in a wavelength range from 380 to 420 nm; a collimator configured to collimate the white light along the main optical axis into a white light beam having a first spatial light distribution with a first Full Width Half Maximum (FWHM1); and a batwing optic configured to shape the violet light along the main optical axis into a batwing shaped light distribution with a maximum intensity at an angle α with respect to the main optical axis, such that the angle α is outside the first FWHM1.

15 Claims, 3 Drawing Sheets

(51) Int. Cl.

| | |
|---|---|
| *A61L 2/10* | (2006.01) |
| *A61L 2/24* | (2006.01) |
| *A61L 9/18* | (2006.01) |
| *A61L 9/20* | (2006.01) |
| *F21V 5/04* | (2006.01) |
| *F21V 23/00* | (2015.01) |

(52) U.S. Cl.

CPC .................. *A61L 9/18* (2013.01); *A61L 9/20* (2013.01); *F21V 23/003* (2013.01); *A61L 2202/11* (2013.01); *A61L 2202/14* (2013.01); *A61L 2209/111* (2013.01); *A61L 2209/12* (2013.01)

(56) References Cited

U.S. PATENT DOCUMENTS

| 8,052,307 | B2 * | 11/2011 | Bak | .................... G02B 19/0066 |
| | | | | 362/249.02 |
| 8,075,157 | B2 * | 12/2011 | Zhang | ................ G02B 19/0061 |
| | | | | 362/249.02 |
| 8,172,433 | B2 * | 5/2012 | Muschaweck | ..... G02B 27/0955 |
| | | | | 362/334 |
| 9,333,274 | B2 * | 5/2016 | Peterson | ................ A61L 2/084 |
| 9,439,989 | B2 * | 9/2016 | Lalicki | ...................... A61L 2/08 |
| 2009/0225543 | A1 | 9/2009 | Jacobson et al. | |
| 2009/0236076 | A1 * | 9/2009 | Min | .................... F28D 15/0275 |
| | | | | 165/151 |
| 2010/0254145 | A1 * | 10/2010 | Yamaguchi | ........ G02B 19/0061 |
| | | | | 362/311.01 |
| 2011/0007513 | A1 * | 1/2011 | Zhang | ................. H10H 20/855 |
| | | | | 362/311.02 |
| 2017/0173195 | A1 | 6/2017 | Stibich et al. | |
| 2018/0283656 | A1 * | 10/2018 | Gommans | .............. F21V 11/06 |
| 2019/0247528 | A1 | 8/2019 | Rodriguez | |
| 2019/0368690 | A1 | 12/2019 | Goldstein | |
| 2021/0379222 | A1 | 12/2021 | Bailey et al. | |
| 2023/0372559 | A1 * | 11/2023 | Kaminski | ................ A61L 2/10 |

* cited by examiner

DISINFECTION LIGHTING DEVICE HAVING BATWING OPTICS

CROSS-REFERENCE TO PRIOR APPLICATIONS

This application is the U.S. National Phase application under 35 U.S.C. § 371 of International Application No. PCT/EP2023/067710, filed on Jun. 28, 2023, which claims the benefit of European Patent Application No. 22183847.7, filed on Jul. 8, 2022. These applications are hereby incorporated by reference herein.

FIELD OF THE INVENTION

The invention relates to a disinfection lighting device configured to provide device light along a main optical axis. The device light comprising one or more of white light, violet light, and/or ultraviolet light. The invention further relates to a lighting system comprising a luminaire and said disinfection lighting device.

BACKGROUND OF THE INVENTION

Societal health is periodically contested by virus outbreaks, such as seasonal symptomatic influenza A/B outbreak, SARS, MERS, COVID-19. Future outbreaks, mutations, epidemics, and pandemics are not excluded. At least partly due to an increasing population, urbanization and people movement, the topic of people health & wellbeing in the built environment is becoming more and more relevant.

These developments have clearly risen the demand for various types of disinfection devices, such as for example disinfection lighting devices (or: light-based disinfection devices). Disinfection lighting devices utilize the germicidal effect of certain wavelengths of light. It is for example known that UV-C radiation has a very strong germicidal effect, but may become harmful to people at certain doses and exposure times.

Another example is violet light having a dominant peak wavelength in a wavelength range from 380 to 420 nm. Such violet light is also used for disinfection; because violet light is much less hazardous to people, compared to said UV-C radiation, and still results in the inactivation of bacteria and/or viruses.

However, even though violet light is within the visible spectrum of a human, thereby enabling people to detect disinfection with violet light, the violet light becomes indistinguishable when combined (or in some cases: polluted) with general white light illumination. This may render the disadvantage that people cannot detect any more whether a disinfection activity is currently operational or not, which is a clear safety risk.

Hence, there is a clear need to enable a more safe integration of the advantageous effects of disinfection lighting, especially utilizing violet light, within the built environment that is also having general lighting arrangements.

SUMMARY OF THE INVENTION

It is an object of the invention to provide an improved disinfection lighting device, which at least alleviates the problems and disadvantages mentioned above. Thereto, the invention provides, a disinfection lighting device configured to provide device light along a main optical axis, said disinfection lighting device comprising: a first solid-state light source configured to emit white light; a second solid-state light source configured to emit violet light having a dominant peak wavelength in a wavelength range from 380 to 420 nm; a collimator configured to collimate said white light along the main optical axis into a white light beam having a first spatial light distribution having a first Full Width Half Maximum (FWHM1); a batwing optic configured to shape said violet light along the main optical axis into a batwing shaped light distribution, wherein the batwing shaped light distribution has a maximum intensity at an angle ($\alpha$) with respect to said main optical axis; wherein said angle ($\alpha$) of a maximum intensity of the batwing shaped light distribution is outside said first Full Width Half Maximum (FWHM1) of the first spatial light distribution of the white light beam.

Hence, the present invention provides a disinfection lighting device (or: alternatively phrased, a light-based disinfection device) configured to provide (or: to emit) device light along (or: centred around) a main optical axis. Said main optical axis may alternatively be defined as a central optical axis. The device light comprises said white light and said violet light. The first solid-state light source emits, in operation, the white light. The second solid-state light source emits, in operation, the violet light. The collimator collimates the white light along the main optical axis into a white light beam having a first spatial light distribution having a first Full Width Half Maximum (FWHM1). The batwing optic shapes the violet light along the main optical axis into a batwing light distribution. The shape of a batwing light distribution is also well known in the art. Alternatively phrased; the batwing optic may shape said violet light along the main optical axis into a violet beam having the batwing light distribution.

The terms 'spatial light distribution', and the 'Full Width Half Maximum' thereof, are well known in the art of lighting. Namely: A spatial light distribution (of a light beam) is typically defined by light intensity as a function of angle (relative to a main optical axis, e.g. the main optical axis being the 0 degrees reference). The 'Full Width Half Maximum' is then the full width of such a spatial light distribution at half of the maximum value. Therefore, a 'Full Width Half Maximum' of a spatial light distribution is typically defined as an angle, or angular range value. Furthermore, the associated term "Half Angle" (HA) is also well known in the art of lighting. An "Half Angle" refers to the angle (within the respective spatial light distribution) at which the light intensity has decreased to half of its maximum value. For example, the Full Width Half Maximum (e.g. a FWHM of 60 degrees) of a bell shaped spatial light distribution may be defined between a first Half Angles (e.g. −30 degrees relative to a main optical axis) and a second Half Angle (e.g. +30 degrees relative to a main optical axis).

Yet in further alternative wording, the feature 'wherein said angle ($\alpha$) of a maximum intensity of the batwing shaped light distribution is outside said first Full Width Half Maximum (FWHM1) of the first spatial light distribution of the white light beam' may also be formulated as: 'wherein said angle ($\alpha$) of a maximum intensity of the batwing shaped light distribution is larger than an angle ($\beta$, or: HA1, HA2) at which the light intensity of the first spatial light distribution of the white light beam has decreased to half of its maximum value.

The second solid-state light source is preferably configured to emit violet light having a dominant peak wavelength in a wavelength range from 400 to 420 nm.

Said angle ($\alpha$) may be phrased throughout the application, for convenience, as violet angle, or batwing angle.

As mentioned, the collimator of the present invention collimates the white light into a white light beam having a first spatial light distribution having a first Full Width Half Maximum (FWHM1); and the batwing optic shapes the violet light along the main optical axis into a batwing shaped light distribution.

Because the angle ($\alpha$) of a maximum intensity of the batwing shaped light distribution is outside said first Full Width Half Maximum (FWHM1) of the first spatial light distribution of the white light beam, the present invention advantageously provides device light having both white light (i.e. suitable for general illumination) and violet light (i.e. suitable for disinfection); but in such a way that the respective spatial light distributions enable light-based disinfection to be performed in the presence of white light without losing the ability to distinguish the violet light from the white light. Namely, due to the batwing shaped light distribution, the violet light will be visible to a human observer as a halo around the white light.

More specifically, the device light comprising the white light beam may render a white light spot, whereas the device light comprising the violet light beam may render a ring-shaped light pattern. As a result, due to the violet light being shaped along the main optical axis into a batwing shaped light distribution, the batwing shaped light distribution is provided (or: projected) as a ring-shaped light pattern around a white light spot provided (or: projected) by said white light beam. Hence, the device light according to the invention renders a violet light with ring-shaped light pattern around a white light spot.

As mentioned, the angle ($\alpha$) of a maximum intensity of the batwing shaped light distribution is outside said first Full Width Half Maximum (FWHM1) of the first spatial light distribution of the white light beam.

When taking said angle ($\alpha$) of the batwing shaped light distribution as a given in certain embodiments, the first Full Width Half Maximum (FWHM1) may be set relative to said angle ($\alpha$) according to the teachings of the present invention. When taking said first Full Width Half Maximum (FWHM1) as a given in certain embodiments, said angle ($\alpha$) of the batwing shaped light distribution may be set relative to said FWHM1 according to the teachings of the present invention. Considering the former, said angle ($\alpha$) of a maximum intensity of the batwing shaped light distribution is preferably larger than 25 degrees, more preferably larger than 40 degrees, most preferably larger than 50 degrees. However, said angle ($\alpha$) may be less than 60 degrees such that glare (resulting from a too wide beam angle for said angle ($\alpha$)) is prevented. In all cases, according to the invention, said angle ($\alpha$) of a maximum intensity of the batwing shaped light distribution is outside said first Full Width Half Maximum (FWHM1) of the first spatial light distribution of the white light beam.

In an embodiment, said angle ($\alpha$) of the maximum intensity of the batwing shaped light distribution may be at least 5 degrees outside said first Full Width Half Maximum (FWHM1). Preferably, said angle ($\alpha$) of the maximum intensity of the batwing shaped light distribution may be at least 10 degrees, more preferably at least 15 degrees, most preferably at least 20 degrees, outside said first Full Width Half Maximum (FWHM1).

Such an embodiment is advantageous, as the violet light may be more distinguishable relative to the white light, when more 'distance' is created between the maximum (or: peak) intensity of the batwing shaped light distribution (occurring at said angle $\alpha$) and the first Full Width Half Maximum (FWHM1) of the first spatial light distribution of the white light beam.

Alternatively phrased, the violet light may be more distinguishable relative to the white light, when more 'distance' is created between the maximum (or: peak) intensity of the batwing shaped light distribution and the Half Angles spanning the FWHM1 of the first spatial light distribution of the white light beam.

In an embodiment, double (or: two times, or: twice) the angle of the maximum intensity of the batwing shaped light distribution may be larger than said first Full Width Half Maximum (FWHM1) plus ten degrees. Alternatively phrased, in more mathematical terms, $2\alpha > \text{FWHM1} + 10$ degrees. Preferably, $2\alpha > \text{FWHM1} + 20$ degrees. Such an embodiment advantageously renders the effect of a higher contrast and/or improved visibility of the violet light with respect to the white light (of the provided device light).

In an embodiment, said first Full Width Half Maximum (FWHM1) may be at most 60 degrees. Said first Full Width Half Maximum may preferably be at most 40 degrees, or more preferably at most 20 degrees, most preferably at most 15 degrees. Such FWHM1 ranges may be suitable for downlighting and/or spotlighting applications. Such an embodiment advantageously renders a more collimated (narrow) beam of white light, thereby preventing glare. This may for example be advantageous for disinfection lighting devices that desire a narrow beam in their implementation, such as for upper-air disinfection where light is desired to be emitted along for example a ceiling surface.

In related embodiments, said first Full Width Half Maximum (FWHM1) may be defined between a first Half Angle (HA1) and a second Half Angle (HA2) of the first spatial light distribution; wherein the first Half Angle (HA1) is at most −30 degrees with respect to the main optical axis; wherein the second Half Angle (HA2) is at most 30 degrees with respect to the main optical axis. Preferably, said first Half Angle (HA1) is at most −12.5 degrees with respect to the main optical axis; wherein the second Half Angle (HA2) is at most 12.5 degrees with respect to the main optical axis.

In aspects, said angle ($\alpha$) of the maximum intensity of the batwing shaped light distribution may be between least 10 degrees and 20 degrees, outside said first Full Width Half Maximum (FWHM1). Hence, the violet light may render a clear aura or halo around the white light.

In an embodiment, the first spatial light distribution may substantially be a symmetric light distribution having a maximum intensity at zero degrees with respect to said main optical axis. Such an embodiment may render optimal (white light) illumination performance. In further embodiments thereof, the first spatial light distribution may substantially be a normal distribution. Said normal distribution may alternatively be phrased as a Gaussian distribution or a Bell Curve. Said first spatial light distribution may thus comprise a maximum, or dominant peak, centered around the main optical axis.

In an embodiment, the angle ($\alpha$) of a maximum intensity of the batwing shaped light distribution may be at most +25 degrees or at most −25 degrees, with respect to the main optical axis. Such an embodiment may render a more collimated (narrow) beam of violet light, thereby preventing glare.

As mentioned, the batwing optic is configured to shape said violet light along the main optical axis into a batwing shaped light distribution. The batwing light distribution according to the invention may, in alternative phrasing, comprise a second Full Width Half Maximum (FWHM2).

According to the invention, alternatively phrased, the second Full Width Half Maximum (FWHM2) may be larger than the first Fill Width Half Maximum (FWHM1). Hence, FWHM2 >FWHM1. Moreover, in some examples, as partly mentioned above, FWHM2 >FWHM1+10 degrees. In some examples, the batwing shaped light distribution may comprise a second Full Width Half Maximum (FWHM2) being at most 50 degrees.

The disinfection performance of the violet light typically increases with lower wavelengths thereof within the violet wavelength range, while the visibility of the violet light typically increases with higher wavelengths thereof within the violet wavelength range. The present invention may optimize the disinfection performance of the violet light with the visibility of the violet light in the presence of the white light. Hence, in an embodiment of the invention, the violet light may have a dominant peak wavelength in a wavelength range from 400 to 415 nm. Preferably, the violet light may have a dominant peak wavelength at the wavelength of 405 nm. Such a specific wavelength of 405 nm may be safe for humans when utilized for disinfection, while still providing an effective germicidal, bactericidal and/or viricidal effect.

In embodiments, the disinfection lighting device may comprise a third solid-state light source configured to emit violet light. Said third solid-state light source may for example be an ultraviolet (UV) light source. Thereby, the device light may further comprise ultraviolet light.

In an embodiment, the light-based disinfection device may comprise a third solid-state light source configured to emit ultraviolet light having a dominant peak wavelength in a wavelength range from 100 to 380 nm; and an optical element configured to collimate and/or shape said ultraviolet light along the main optical axis into an ultraviolet light beam. Even though violet light is effective in inactivating pathogens such as bacteria, the ultraviolet light may add effectiveness in inactivating viral matter. Such an embodiment may therefore improve the germicidal effect, or disinfection performance, of the disinfection lighting device according to the invention.

In a first related embodiment, said optical element may be configured to collimate said ultraviolet light along the main optical axis into an ultraviolet light beam having a third spatial light distribution; wherein the third spatial light distribution may be substantially a symmetric light distribution having a maximum intensity at zero degrees with respect to said main optical axis. In examples, the optical element may be the collimator.

Such an embodiment may be advantageous: Because the batwing shaped light distribution of the violet light renders lower intensity of violet light at angles closer to the main optical axis and thereby renders less disinfection performance closer to the main optical axis, the substantially symmetric third spatial light distribution of ultraviolet light having a maximum intensity at zero degrees with respect to said main optical axis may provide a disinfection performance closer to the main optical axis, thereby resolving and/or complementing the lesser disinfection performance of the violet light closer to the main optical axis. Hence, the device light comprising the white light, the violet light, and the ultraviolet light, provides a (spatial light distribution with an) improved disinfection performance. In other words, the ultraviolet light compensates for the violet light not being present (to a certain degree) within the centre of the spatial light distribution of the white light and the first (white light) spatial light distribution.

In a second related embodiment, said optical element may be configured to shape said ultraviolet light along the main optical axis into a batwing shaped light distribution having a maximum intensity at a further angle with respect to said main optical axis; wherein said further angle is within 10 degrees of said angle ($\alpha$) of the maximum intensity of the batwing shaped light distribution of the violet light.

In examples, said further angle may be within 8 degrees, preferably within 5 degrees, most preferably within 3 degrees, of said angle ($\alpha$) of the maximum intensity of the batwing shaped light distribution of the violet light. In examples, the further angle may be identical to the angle ($\alpha$) of the maximum intensity of the batwing shaped light distribution of the violet light. In examples, the optical element may be said batwing optic.

Such an embodiment may be advantageous, because due to the ultraviolet light also being shaped into a batwing shaped light distribution, that is being within 10 degrees and/or identical to the batwing shaped light distribution of the violet light, the ultraviolet light may complement the violet light in disinfection. Moreover, the violet light may also be an indicator for the (more hazardous) ultraviolet light, that is otherwise invisible to a human. Hence, the violet light may in such embodiments and examples visualize the ultraviolet light.

Additionally or alternatively, in an embodiment, the ultraviolet light may have a dominant peak wavelength in a wavelength range from 100 to 280 nm. Hence, the ultraviolet light may comprise UV-C light.

In additional or alternative examples, the ultraviolet light may have a dominant peak wavelength in a wavelength range from 280 to 315 nm. Hence, the ultraviolet light may comprise UV-B light.

In an embodiment, the light-based disinfection device the disinfection lighting device may comprise a controller; wherein the controller is configured to individually control a light intensity of the first solid-state light source, the second solid-state light source, and/or the third solid-state light source.

In a related embodiment, the controller may be configured to obtain a control signal; wherein the controller may be configured to control the at least one second solid-state light source to provide the violet light upon obtaining said control signal.

In a related embodiment, wherein the disinfection lighting device may comprise a sensor for sensing a parameter of a person; wherein the sensor is configured to generate the control signal upon sensing the parameter of said person, and convey said control signal to the controller. In an embodiment, said parameter may be the presence of a person, and/or the motion of a person, and/or the proximity of a person. Said sensor may for example be at least one of: a camera, a PIR sensor, a thermopile array sensor, a Single Pixel Thermopile, a pressure sensor, a microwave sensor, a radar sensor, a RF transceiver enabling RF-based sensing.

Such an embodiment may enhance safety, because when e.g. the presence of a person is detected, the violet light having the batwing shaped light distribution may be provided with the white light beam, thereby rendering a (light-based) disinfection activity in the presence of the person, which disinfection activity the person may visually detect (or: observe).

In an embodiment, said sensor comprises a detection region, said device light comprises a main illumination region (or: footprint), wherein the detection region of said sensor is larger than said main illumination region. This enables that a person may visually detect the device light due to the violet light and the white light, before entering the main illumination region and/or footprint of said light.

In an embodiment, the controller may be configured to control the at least one second solid-state light source to provide the violet light with a pulsed intensity profile having a pulse frequency between 0.05 and 20 Hertz. Such an embodiment may be advantageous, as a dynamic violet light (i.e. having a pulsed intensity profile) may enhance the distinguishing of the violet light from the white light. Said pulse frequency may preferably be between 0.2 and 5 Hertz.

Furthermore, the controller may, while controlling the at least one second solid-state light source to provide the violet light with said pulsed intensity profile, control the at least one first solid-state light source to provide the white light (and resulting white light beam) with a steady (or: static, or: constant) intensity profile.

In aspects, the light-based disinfection device may comprise a presence sensor, motion sensor, and/or a proximity sensor; wherein the disinfection lighting device may be further configured to provide the device light for a predetermined duration and/or a predetermined intensity based on a presence of a person detected by said presence sensor, motion sensor, and/or a proximity sensor; and wherein said device light is not provided (e.g. switched off) when the person is within a threshold distance from the proximity sensor.

Said first solid-state light source may be at least one first solid-state light source. Said second solid-state light source may be at least one second solid-state light source. Said third solid-state light source may be at least one third solid-state light source. The solid-state light sources according to the invention may for example be a LED light source.

In aspects, said violet light may be more prominent. Hence, in aspects, the maximum intensity of the batwing shaped light distribution of the violet light may be at least a factor 1.5 higher than the maximum intensity of the first spatial light distribution of the white light (beam), for example a factor 2 higher. This may make the violet light more visible within the white light, as the contrast may be improved. Moreover, while dimming the white light with respect to the violet light, said factor may remain constant.

It is further an object of the invention to provide an improved lighting system, which at least alleviates the problems and disadvantages mentioned above. Thereto, the invention provides a lighting system comprising a luminaire housing and said disinfection lighting device, wherein the luminaire housing comprises said disinfection lighting device.

In further embodiments, the lighting system may be one of a spotlight, an LED panel, an LED bulb, a downlight. Thereby, advantages and/or embodiments applying to the disinfection lighting device according to the invention may mutatis mutandis apply to said lighting system according to the invention.

It is further an object of the invention to provide an improved method which at least alleviates the problems and disadvantages mentioned above. Thereto, the invention provides a method of providing device light along a main optical axis, wherein the method comprises: emitting white light; emitting violet light having a dominant peak wavelength in a wavelength range from 380 to 420 nm; collimating said white light along the main optical axis into a white light beam having a first spatial light distribution having a first Full Width Half Maximum (FWHM1); shaping said violet light along the main optical axis into a batwing shaped light distribution, wherein the batwing shaped light distribution has a maximum intensity at an angle ($\alpha$) with respect to said main optical axis; wherein said angle of a maximum intensity of the batwing shaped light distribution is outside said first Full Width Half Maximum (FWHM1) of the first spatial light distribution of the white light beam. Thereby, advantages and/or embodiments applying to the disinfection lighting device according to the invention may mutatis mutandis apply to said method according to the invention.

In aspects, alternatively phrased, the invention provides a light-based disinfection device for emitting device light along a main optical axis, wherein the light-based disinfection device comprises: at least one first solid-state light source configured to provide white light; at least one second solid-state light source configured to provide violet light having a dominant peak wavelength in a wavelength range from 380 to 420 nm; a collimator configured to collimate said white light along the main optical axis into a white light beam having a first spatial light distribution having a first Full Width Half Maximum (FWHM); a batwing optic configured to shape said violet light along the main optical axis into a batwing shaped light distribution; wherein at least one peak intensity of the batwing shaped light distribution is at an angle outside said first Full Width Half Maximum (FWHM) of the first spatial light distribution of the white light beam.

BRIEF DESCRIPTION OF THE DRAWINGS

The invention will now be further elucidated by means of the schematic non-limiting drawings.

DETAILED DESCRIPTION OF THE EMBODIMENTS

Violet light is known to provide a germicidal effect while being safe to humans. Violet light may typically inactivate bacteria, but also viruses. Therefore, violet light is regularly used for (light-based) disinfection.

However, even though violet light is within the visible spectrum of a human, thereby enabling people to detect disinfection with violet light, the violet light becomes indistinguishable when combined (or in some cases: polluted) with general white light illumination. This may render the disadvantage that people cannot detect any more whether a disinfection activity is currently operational or not, which is a clear safety risk.

There is a clear need to enable a safer integration of the advantageous effects of disinfection lighting, especially utilizing violet light, within the built environment that is also having general lighting arrangements, that typically emit white light.

This need is met by the lighting system, the disinfection lighting device, and associated method according to the present invention. The present invention will be explained and elucidated with reference to the appended figures.

Figure 1:
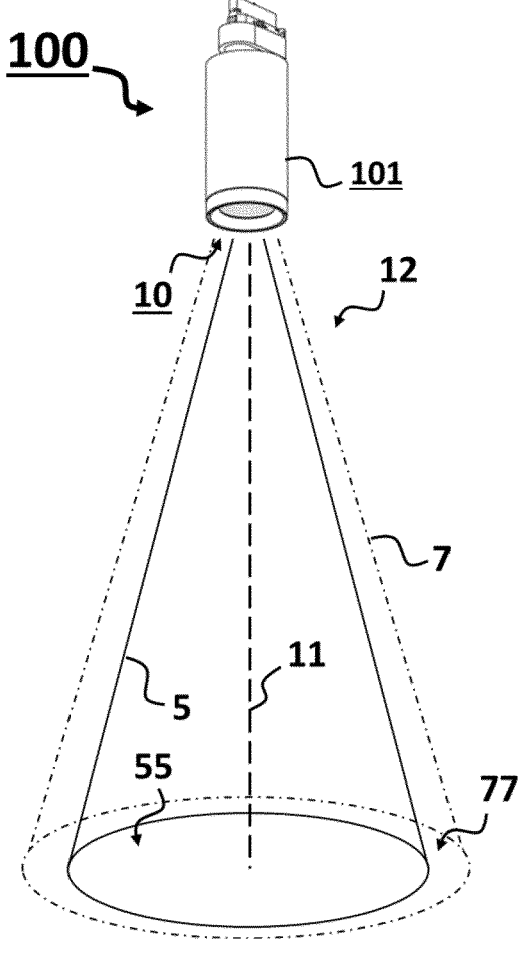
FIG. 1 depicts schematically an embodiment of a lighting system according to the invention.

FIG. 1 depicts schematically, by non-limiting example, an embodiment of a lighting system 100 according to the invention. The lighting system 100 comprises a luminaire housing 101 and a disinfection lighting device 10. The luminaire housing 101 is comprising (or: housing) the disinfection lighting device 10.

Figure 2:
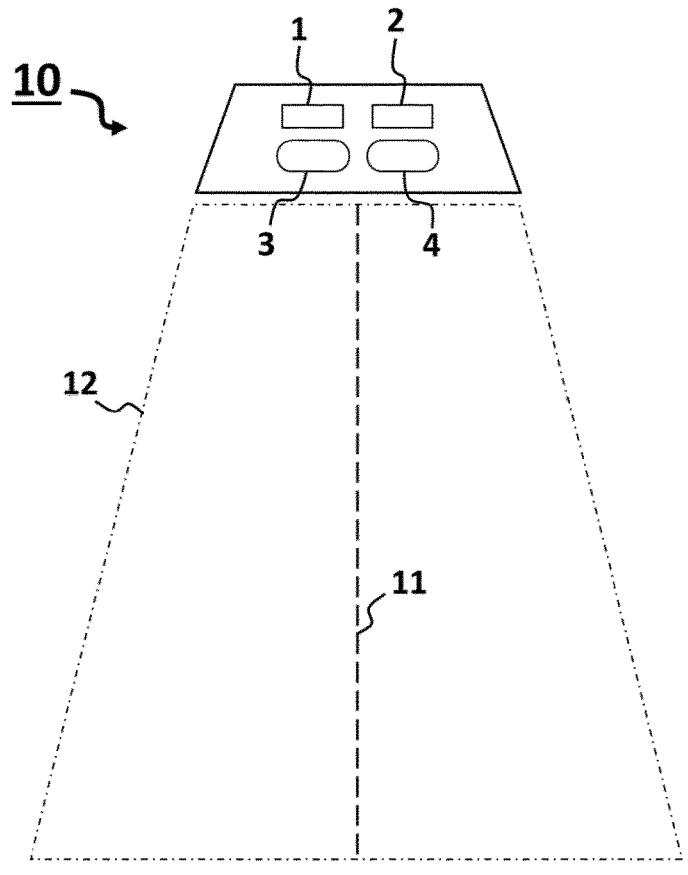
FIG. 2 depicts schematically an embodiment of a disinfection lighting device according to the invention.
Figure 2:
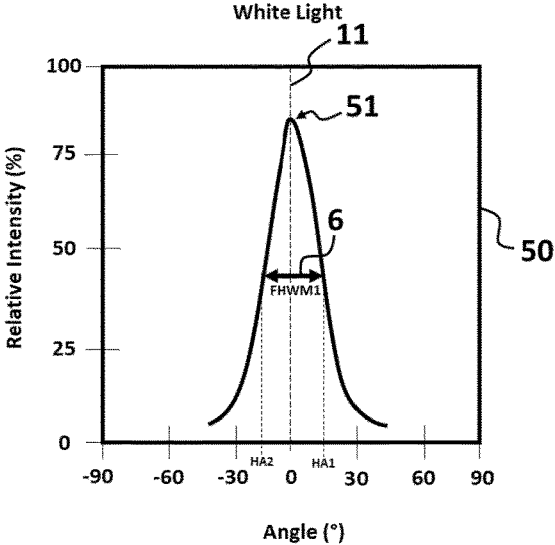
Figure 2:
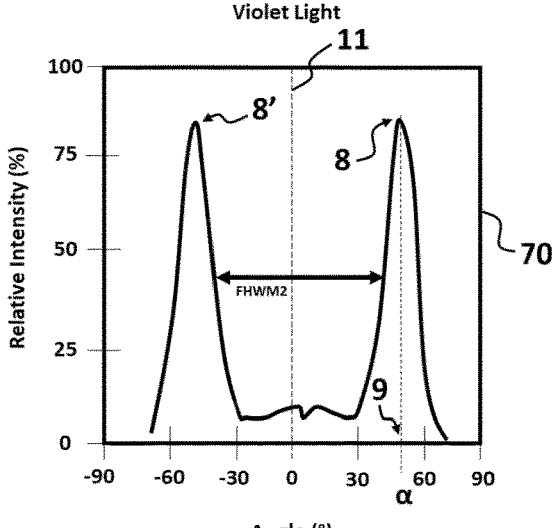
Figure 3:
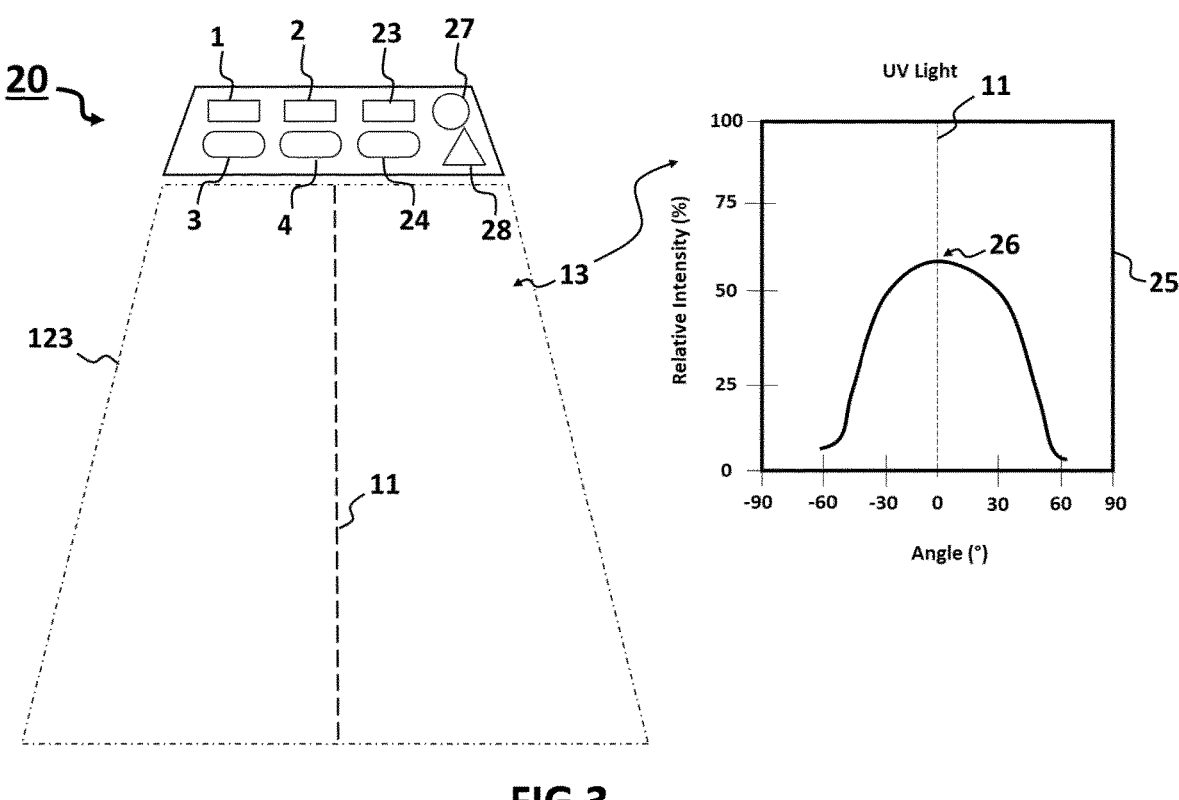
FIG. 3 depicts schematically an embodiment of a disinfection lighting device according to the invention.

Said disinfection lighting device 10 may for example be the disinfection lighting device 10 as schematically depicted in FIG. 2, or alternatively the disinfection lighting device 30 as schematically depicted in FIG. 3, as described in more detail below.

Here, the lighting system 100 is a spotlight. Alternatively, the lighting system may be one of a downlight, a LED panel, an LED bulb, a troffer luminaire, a recessed ceiling luminaire, an upper air disinfection luminaire configured to provide device light substantially parallel to a surface, a high-bay luminaire.

Referring to FIG. 1, the disinfection lighting device 10 of the lighting system 100 provides device light 12 along a main optical axis 11. Here, the device light 12 comprises white light 5 and violet light 7.

Still referring to FIG. 1, the white light 5 comprises a main illumination region that renders a white light footprint area 55 onto a surface below the spotlight 100. The violet light 7 comprises a main illumination region that renders a violet light footprint area 77 onto said surface below the spotlight 100. More specifically, the device light 12 according to the invention renders a violet light 7 with ring-shaped light pattern around a spot of white light 5.

FIG. 2 depicts schematically, by non-limiting example, an embodiment of a disinfection lighting device 10 according to the invention. As mentioned, the disinfection lighting system 10 may be part of the lighting system depicted in FIG. 1.

The disinfection lighting device 10 comprises a first solid-state light source 1. The first solid-state light source 1 is configured to emit, in operation, white light 5. White light 5 is known to a person skilled in the art. Said white light 5 may be referred to as visible light. The white light 5 may have a spectrum within the visible spectrum of a human.

The disinfection lighting device 10 further comprises a second solid-state light source 2. The second solid-state light source 2 is configured to emit, in operation, violet light 7. The violet light 7 has a dominant peak wavelength in a wavelength range from 380 to 420 nm. Violet light 7 may be safe for humans when utilized for disinfection, while still providing an effective germicidal, bactericidal and/or viricidal effect.

The disinfection performance of the violet light 7 typically increases with lower wavelengths thereof within the violet wavelength range, while the visibility of the violet light 7 typically increases with higher wavelengths thereof within the violet wavelength range. The present invention may optimize the disinfection performance of the violet light 7 with the visibility of the violet light 7 in the presence of the white light 5. Hence, alternatively, in other preferred embodiments, the violet light 7 may have a dominant peak wavelength in a wavelength range from 400 to 415 nm, for example 405 nm.

Still referring to FIG. 2, the disinfection lighting device 10 is configured to provide device light 12 along (or: centred around) a main optical axis 11. Said main optical axis 11 may alternatively be defined as a central optical axis. Here, the device light 12 comprises the white light 5 and the violet light 7.

The disinfection lighting device 10 further comprises a collimator 3. The collimator collimates the white light 5 (comprises within the device light 12) along the main optical axis 11 into a white light beam having a first spatial light distribution 50. The first spatial light distribution 50 has a first Full Width Half Maximum 6 (FWHM1). The white light beam may also be referenced with numeral 5.

The terms 'spatial light distribution', and the 'Full Width Half Maximum' thereof, are well known in the art of lighting. Namely: A spatial light distribution (of a light beam) is typically defined by light intensity as a function of angle (relative to a main optical axis 11, e.g. the main optical axis 11 being the 0 degrees reference). The 'Full Width Half Maximum' is then the full width of such a spatial light distribution at half of the maximum value. Therefore, a 'Full Width Half Maximum' of a spatial light distribution is typically defined as an angle, or angular range value. Furthermore, the associated term "Half Angle" (HA) is also well known in the art of lighting. An "Half Angle" refers to the angle (within the respective spatial light distribution) at which the light intensity has decreased to half of its maximum value.

Still referring to FIG. 2, the first spatial light distribution 50 of the white light beam 5 has a first Full Width Half Maximum 6 (FWHM1). Here, the first Full Width Half Maximum 6 (FWHM1) is at most 60 degrees, namely 30 degrees, spanning between a first Half Angle (HA1) of 15 degrees and a second Half Angle (HA2) of −15 degrees with respect to the main optical axis 11. Alternatively, said first Full Width Half Maximum (FWHM1) may be at most 25 degrees. Yet alternatively, said first Full Width Half Maximum (FWHM1) may be 60 degrees, spanning between the angles of −30 degrees and +30 degrees with respect to said main optical axis.

Moreover, the first spatial light distribution 50 of the white light beam 5 is substantially a symmetrical light distribution having the maximum intensity 51 at zero degrees with respect to said main optical axis 11. Hence, the white light 5 may be collimated into a narrow and symmetrical white light beam, thereby preventing glare, and providing a desired white light distribution for a spotlight (or: point source of light).

Still referring to FIG. 2, the disinfection lighting device 10 further comprises a batwing optic 4. The batwing optic 4 shapes the violet light 7 of the second solid-state light source 2 along the main optical axis 11 into a batwing shaped light distribution 70. The shape of a batwing light distribution is typically known in the art. Here, the batwing shaped light distribution 70 has a maximum intensity 8, 8' at an angle 9 (α) with respect to said main optical axis 11. Said angle 9 (α) is at +50 degrees (and/or at −50 degrees) with respect to said main optical axis 11.

More specifically, said maximum intensity may either be a first maximum intensity 8 of the batwing shape having a positive angle 9 (α) with respect to said main optical axis 11, i.e. at +50 degrees; or the counterpart, a second maximum intensity 8' of the batwing shape having a negative angle, i.e. at −50 degrees, this maximum being referred to with numeral 8'.

Still referring to FIG. 2, according to the present invention, the angle 9 (α) of said maximum intensity 8 of the batwing shaped light distribution 70 is outside said first Full Width Half Maximum 6 (FWHM1) of the first spatial light distribution 50 of the white light beam. Namely, the angle 9 (α) of said maximum intensity 8 of the batwing shaped light distribution 70 is at +50 degrees (or: −50 degrees) with respect to said main optical axis 11, whereas said first Full Width Half Maximum 6 (FWHM1) is spanned between −15 degrees and +15 degrees with respect to said main optical axis 11. Hence, the angle 9 (α) of said maximum intensity 8 of the batwing shaped light distribution 70 is clearly outside said first Full Width Half Maximum (FWHM1).

Because the angle 9 (α) of the maximum intensity 8 of the batwing shaped light distribution 70 is outside said first Full Width Half Maximum 6 (FWHM1) of the first spatial light distribution 50 of the white light beam, the present invention advantageously provides device light 12 having both white light 5 (i.e. suitable for general illumination) and violet light 7 (i.e. suitable for disinfection); but in such a way that the respective spatial light distributions 50, 70 enable light-based disinfection to be performed in the presence of white light 5 without losing the ability to distinguish the violet light 7 from the white light 5.

Namely, due to the batwing shaped light distribution 70, the violet light 7 will be visible to a human observer as for example a halo around the white light 5. This is also depicted in FIG. 1 and the corresponding footprints 55 and 77 of respectively the white light 5 and the violet light 7.

More specifically, considering the device light 12 provided by the disinfection lighting device 10, the violet light 7 may be more distinguishable relative to the white light 5, when more 'distance' is created between the maximum 8, 8' intensity of the batwing shaped light distribution 70, which are occurring at said angle 9 (α), and the first Full Width Half Maximum 6 (FWHM1) of the first spatial light distribution 50 of the white light beam. Hence, in the present embodiment, as depicted in FIG. 2, albeit not necessary, the angle 9 (α) of said maximum intensity 8 of the batwing shaped light distribution 70 is at least 20 degrees outside said First Full Width Half Maximum 6 (FWHM1).

In an alternative example, the angle of a maximum intensity of the batwing shaped light distribution may be at most+25 degrees and/or at most −25 degrees, with respect to said main optical axis. Such an embodiment may render a more collimated (narrow) beam of violet light, thereby preventing glare. The first Full Width Half Maximum (FWHM1) should therefore be smaller than said angles −25 degrees and/or +25 degrees, with respect to said main optical axis.

In an alternative example, double the angle 9 (α) of the maximum intensity of the batwing shaped light distribution 70 may be larger than said first Full Width Half Maximum 6 (FWHM1) plus ten degrees. In FIG. 2, the FWHM1+10 degrees is a total of 40 degrees. Hence, said angle α may at least be at 20 degrees with respect to said main optical axis 11. (Alternatively phrased, in more mathematical terms, 2α>FWHM1+10 Degrees. Such an embodiment advantageously renders the effect of a higher contrast and/or improved visibility of the violet light with respect to the white light (of the provided device light).

Alternatively, the bating shaped light distribution may comprise a second Full Width Half Maximum (FWHM2). According to the invention, the second Full Width Half Maximum (FWHM2) may be outside the First Full Width Half Maximum (FWHM1). Hence, FWHM2 >FWHM1. Moreover, in some alternative examples, as partly mentioned above, FWHM2 >FWHM1+10 Degrees.

FIG. 3 depicts schematically, by non-limiting example, an embodiment of a disinfection lighting device 20 according to the invention, which is similar to the disinfection lighting device 10 depicted in FIG. 2, but in addition comprises a third solid-state light source 23, an optical element 24, optionally a controller 27 and sensor 28. The disinfection lighting device 20 is configured to provide device light 123. Here, the device light 123 comprises white light 5, violet light 7, and also ultraviolet light 13.

The ultraviolet light 13 may have a dominant peak wavelength in a wavelength range from 100 to 280 nm. Hence, the ultraviolet light 13 may comprise UV-C light. In additional or alternative examples, the ultraviolet light 13 may have a dominant peak wavelength in a wavelength range from 280 to 315 nm. Hence, the ultraviolet light 13 may comprise UV-B light.

Further referring to FIG. 3, The third solid-state light source 23 is configured to emit, in operation, ultraviolet light 13 having a dominant peak wavelength in a wavelength range from 100 to 380 nm. The optical element 24 is configured to collimate and/or shape said ultraviolet light 13 along the main optical axis 11 into an ultraviolet light beam. The ultraviolet light beam has a third spatial light distribution 25. Here, the third spatial light distribution 25 is a substantially symmetric light distribution having a (single) maximum intensity 26 at zero degrees with respect to said main optical axis 11. Here, the third spatial light distribution 25 is different from the first spatial light distribution 50 of the white light 5, but may alternatively be the same.

Namely, in alternative embodiments, the optical element 24 may at least partly be the same as the collimator 3. In such alternative examples, the third spatial light distribution of the ultraviolet light 13 may be the same as the first spatial light distribution 50 of the white light (beam) 5.

The embodiment depicted in FIG. 3, and said alternative embodiments, may be advantageous: Because the batwing shaped light distribution 70 of the violet light 7 renders lower intensity of violet light 7 at angles closer to the main optical axis 11 and thereby renders less disinfection performance closer to the main optical axis 11, the substantially symmetric third spatial light distribution 25 of ultraviolet light 13 having a maximum intensity 26 at zero degrees with respect to said main optical axis 11 may provide a disinfection performance closer to the main optical axis 11, thereby resolving and/or complementing the lesser disinfection performance of the violet light 7 closer to the main optical axis 11.

Hence, the device light 123 comprising the white light 5, the violet light 7, and the ultraviolet light 13, provides a (spatial light distribution with an) improved disinfection performance. In other words, the ultraviolet light 13 compensates for the violet light 7 not being present (to a certain degree) within the centre of the spatial light distribution of the white light 5 and the first (white light) spatial light distribution 50.

Alternatively, the optical element 24 may at least partly be the same as the batwing optic 4. In such examples, the optical element may shape the ultraviolet light 13 along the main optical axis 11 into a batwing shaped light distribution having a maximum intensity at a further angle with respect to said main optical axis 11. Said further angle may be at most 10 degrees from said angle 9 (α) of the maximum intensity of the batwing shaped light distribution 70 of the violet light 7, as mentioned in the discussion of FIG. 2. Moreover, said further angle may be the same as the angle 9 (α) of the maximum intensity of the batwing shaped light distribution 70 of the violet light 7. Hence, the third spatial light distribution of the ultraviolet light 13 may be similar or the same as the batwing shaped light distribution 70. Such an embodiment may be advantageous, because due to the ultraviolet light also being shaped into a batwing shaped light distribution, that is being within 10 degrees and/or identical to the batwing shaped light distribution of the violet light, the ultraviolet light may complement the violet light in disinfection. Moreover, the violet light may also be an indicator for the (more hazardous) ultraviolet light, that is otherwise invisible to a human. Hence, the violet light may in such embodiments and examples visualize the ultraviolet light.

Still referring to FIG. 3, as mentioned, the disinfection lighting device 20 further comprises optionally a controller 27 and sensor 28. The controller 27 is configured to individually control a light intensity of the first solid-state light source 1, the second solid-state light source 2, and/or the third solid-state light source 23. The controller is also configured to obtain a control signal. This may be either the controller receiving or retrieving a control signal via a wired and/or wireless communication modality. The controller thereby controls the second solid-state light source 2 to provide the violet light 7 upon obtaining said control signal. Here, said control signal may be conveyed to the controller from a sensor device. Alternatively, said control signal may be conveyed to the controller from a user control device, such as a remote control device, user interface, smartphone device, tablet device, a computer, a portable smart device, etc.

Namely, the disinfection lighting device 20 comprises a sensor 28 for sensing a parameter of a person. Said parameter may be the presence of a person, and/or the motion of a person, and/or the proximity of a person. Alternatively, said parameter may be a user preference, a user activity of the person, or user condition. Here, said parameter is the presence of a person. The sensor 28 is thereby configured to generate the control signal upon sensing the parameter of said person, and convey said control signal to the controller 27. The controller 27 will then control the second solid-state light source 2 to provide the violet light 7. Said sensor may for example be at least one of: a camera, a PIR sensor, a thermopile array sensor, a Single Pixel Thermopile, a pressure sensor, a microwave sensor, a radar sensor, a RF transceiver enabling RF-based sensing.

Such operation may enhance safety, because when e.g. the presence of a person is detected, the violet light having the batwing shaped light distribution may be provided with the white light beam, thereby rendering a (light-based) disinfection activity in the presence of the person, which disinfection activity the person may visually detect (or: observe).

Figure 4:
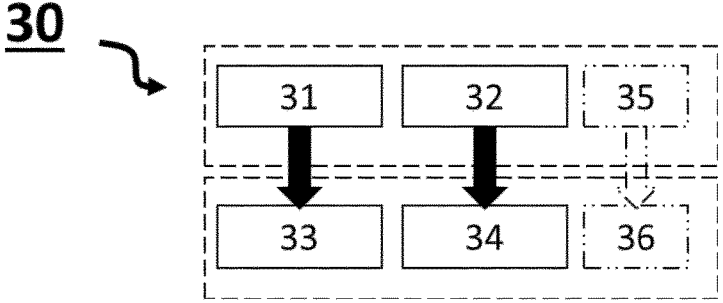
FIG. 4 depicts schematically an embodiment of a method according to the invention.

FIG. 4 depicts schematically, by non-limiting example, a method 30 of providing device light along a main optical axis, according to the invention. The method 30 may be performed by the lighting system 100 and/or the disinfection lighting device 10, 20 according to the invention.

The method 30 comprises the step 31 of emitting white light, and step 32 of emitting violet light having a dominant peak wavelength in a wavelength range from 380 to 420 nm. The method further comprises the step 33 of collimating said white light along the main optical axis into a white light beam having a first spatial light distribution having a first Full Width Half Maximum (FWHM1). The method further comprises the step 34 of shaping said violet light along the main optical axis into a batwing shaped light distribution, wherein the batwing shaped light distribution has a maximum intensity at an angle ($\alpha$) with respect to said main optical axis. The method is further characterized in that said angle of a maximum intensity of the batwing shaped light distribution is outside said first Full Width Half Maximum (FWHM1) of the first spatial light distribution of the white light beam. The first spatial light distribution being a substantially symmetrical light distribution having a maximum intensity at the zero angle with respect to said main optical axis.

The method 30 may optionally comprise the step of emitting ultraviolet light 35, and the step of collimating and/or shaping 36 the ultraviolet light into a third spatial light distribution. The third spatial light distribution being a substantially symmetrical light distribution having a maximum intensity at the zero angle with respect to said main optical axis.

The invention claimed is:

1. A disinfection lighting device configured to provide device light along a main optical axis, said disinfection lighting device comprising:
  a first solid-state light source configured to emit white light;
  a second solid-state light source configured to emit violet light having a dominant peak wavelength in a wavelength range from 380 to 420 nm;
  a collimator configured to collimate said white light along the main optical axis into a white light beam having a first spatial light distribution having a first Full Width Half Maximum;
  a batwing optic configured to shape said violet light along the main optical axis into a batwing shaped light distribution, wherein the batwing shaped light distribution has a maximum intensity at an angle with respect to said main optical axis;
  wherein said angle of a maximum intensity of the batwing shaped light distribution is outside said first Full Width Half Maximum of the first spatial light distribution of the white light beam.

2. The disinfection lighting device according to claim 1, wherein said angle of the maximum intensity of the batwing shaped light distribution is at least 10 degrees outside said first Full Width Half Maximum.

3. The disinfection lighting device according to claim 1, wherein double the angle of the maximum intensity of the batwing shaped light distribution is larger than said first Full Width Half Maximum plus ten degrees.

4. The disinfection lighting device according to claim 1, wherein said first Full Width Half Maximum is at most 60 degrees, preferably at most 25 degrees.

5. The disinfection lighting device according to claim 1, wherein the first spatial light distribution is substantially a symmetric light distribution having a maximum intensity at zero degrees with respect to said main optical axis.

6. The disinfection lighting device according to claim 1, wherein the violet light has a dominant peak wavelength in a wavelength range from 400 to 415 nm.

7. The disinfection lighting device according to claim 1, wherein the disinfection lighting device is a spotlight, a LED panel, or a LED bulb.

8. The disinfection lighting device according to claim 1, wherein the light-based disinfection device comprises a third solid-state light source configured to emit ultraviolet light having a dominant peak wavelength in a wavelength range from 100 to 380 nm; and
  an optical element configured to collimate and/or shape said ultraviolet light along the main optical axis into an ultraviolet light beam.

9. The disinfection lighting device according to claim 8, wherein said optical element is configured to collimate said ultraviolet light along the main optical axis into an ultraviolet light beam having a third spatial light distribution;
  wherein the third spatial light distribution is substantially a symmetric light distribution having a maximum intensity at zero degrees with respect to said main optical axis.

10. The disinfection lighting device according to claim 8, wherein said optical element is configured to shape said ultraviolet light along the main optical axis into a batwing shaped light distribution having a maximum intensity at a further angle with respect to said main optical axis;

wherein said further angle is within 10 degrees of said angle of the maximum intensity of the batwing shaped light distribution of the violet light.

11. The disinfection lighting device according to claim 8, wherein the ultraviolet light has a dominant peak wavelength in a wavelength range from 100 to 280 nm.

12. The disinfection lighting device according to claim 1, wherein the disinfection lighting device comprises a controller;

wherein the controller is configured to individually control a light intensity of the first solid-state light source, the second solid-state light source, and/or the third solid-state light source.

13. The disinfection lighting device according to claim 12, wherein the controller is configured to control the at least one second solid-state light source to provide the violet light with a pulsed intensity profile having a pulse frequency between 0.05 and 20 Hertz.

14. The disinfection lighting device according to claim 12, wherein the controller is configured to obtain a control signal;

wherein the controller is configured to control the second solid-state light source to provide the violet light upon obtaining said control signal.

15. The disinfection lighting device according to claim 14, wherein the light-based disinfection device comprises a sensor for sensing a presence of a person;

wherein the sensor is configured to generate the control signal upon sensing the presence of said person, and convey said control signal to the controller.

\* \* \* \* \*